(12) United States Patent
Tan

(10) Patent No.: US 6,485,667 B1
(45) Date of Patent: Nov. 26, 2002

(54) PROCESS FOR MAKING A SOFT, STRONG, ABSORBENT MATERIAL FOR USE IN ABSORBENT ARTICLES

(75) Inventor: Erol Tan, Zutphen (NL)

(73) Assignee: Rayonier Products and Financial Services Company, Fernandina Beach, FL (US)

(*) Notice: Subject to any disclaimer, the term of this patent is extended or adjusted under 35 U.S.C. 154(b) by 0 days.

(21) Appl. No.: 09/390,018

(22) Filed: Sep. 3, 1999

Related U.S. Application Data

(63) Continuation-in-part of application No. PCT/US98/00639, filed on Jan. 15, 1998, which is a continuation-in-part of application No. 08/948,987, filed on Oct. 10, 1997, now Pat. No. 5,916,670, which is a continuation-in-part of application No. 08/784,536, filed on Jan. 17, 1997, now Pat. No. 5,866,242.

(51) Int. Cl.[7] .............................. A61F 13/15; B27N 3/04
(52) U.S. Cl. ........................ 264/510; 264/518; 264/112; 264/121; 264/122
(58) Field of Search ................................. 264/510, 517, 264/518, 109, 112, 113, 122, 121, 123

(56) References Cited

U.S. PATENT DOCUMENTS

| | | |
|---|---|---|
| 2,905,568 A | 9/1959 | Burgeni |
| 2,952,260 A | 9/1960 | Burgeni |
| 2,955,641 A | 10/1960 | Burgeni |
| 3,017,304 A | 1/1962 | Burgeni |
| 3,612,055 A | 10/1971 | Mesek |
| 3,730,184 A | 5/1973 | Mesek |
| 3,763,863 A | 10/1973 | Mesek et al. |
| 3,768,480 A | 10/1973 | Mesek et al. |
| 3,837,343 A | 9/1974 | Mesek |
| 3,938,522 A | 2/1976 | Repke |
| 3,965,904 A | 6/1976 | Mesek et al. |
| 4,102,340 A | 7/1978 | Mesek et al. |
| 4,186,165 A | 1/1980 | Aberson et al. |
| 4,217,901 A | 8/1980 | Bradstreet et al. |
| 4,259,387 A | 3/1981 | Mesek |
| 4,260,443 A | 4/1981 | Lindsay et al. |
| 4,282,874 A | 8/1981 | Mesek |
| 4,412,036 A | 10/1983 | Pedersen et al. |
| 4,426,258 A | 1/1984 | Browning |
| 4,467,012 A | 8/1984 | Pedersen et al. |

(List continued on next page.)

FOREIGN PATENT DOCUMENTS

| | | |
|---|---|---|
| EP | 0 763 364 A2 | 3/1997 |
| GB | 2272916 A | 1/1994 |
| JP | 58-36452 | 3/1983 |
| WO | WO 95/20066 | 7/1995 |
| WO | WO 00/69383 | 11/2000 |

OTHER PUBLICATIONS

English language translation of EP 1032342 B1.

Primary Examiner—Mathieu D. Vargot
(74) Attorney, Agent, or Firm—Wood, Phillips, Katz, Clark & Mortimer

(57) ABSTRACT

A process is provided for making an absorbent material. A web is formed with at least one layer of a mixture of cellulosic fibers and superabsorbent material. The moisture content of the web is increased so as to increase the web density. Then, the web is compacted at an elevated temperature to further increase the web density and to effect hydrogen bonding within the web.

4 Claims, 4 Drawing Sheets

U.S. PATENT DOCUMENTS

| | | |
|---|---|---|
| 4,500,315 A | 2/1985 | Pieniak et al. |
| 4,537,590 A | 8/1985 | Pieniak et al. |
| 4,540,454 A | 9/1985 | Pieniak et al. |
| 4,551,142 A | 11/1985 | Kopolov |
| 4,573,988 A | 3/1986 | Pieniak et al. |
| 4,600,458 A | 7/1986 | Kramer et al. |
| 4,604,313 A | 8/1986 | McFarland et al. |
| 4,605,401 A | 8/1986 | Chmelir |
| 4,605,402 A | 8/1986 | Iskra |
| 4,610,678 A | 9/1986 | Weisman et al. |
| 4,640,810 A | 2/1987 | Laursen et al. |
| 4,655,757 A | 4/1987 | McFarland et al. |
| 4,670,011 A | 6/1987 | Mesek |
| 4,673,402 A | 6/1987 | Weisman et al. |
| 4,699,619 A | 10/1987 | Bernardin |
| RE32,649 E | 4/1988 | Brandt et al. |
| 4,798,603 A | 1/1989 | Meyer et al. |
| 4,820,295 A | 4/1989 | Chapas et al. |
| 4,834,735 A | 5/1989 | Alemany et al. |
| 4,904,249 A | 2/1990 | Miller et al. |
| 4,921,643 A | 5/1990 | Walton et al. |
| 4,927,582 A | 5/1990 | Bryson |
| 4,960,477 A | 10/1990 | Mesek |
| 4,988,344 A | 1/1991 | Reising et al. |
| 5,019,063 A | 5/1991 | Marsan et al. |
| 5,037,409 A | 8/1991 | Chen et al. |
| 5,047,023 A | 9/1991 | Berg |
| 5,061,259 A | 10/1991 | Goldman et al. |
| 5,102,585 A | 4/1992 | Pieper et al. |
| 5,149,335 A | 9/1992 | Kellenberger et al. |
| 5,156,902 A | 10/1992 | Pieper et al. |
| 5,217,445 A | 6/1993 | Young et al. |
| 5,248,309 A | 9/1993 | Serbiak et al. |
| 5,262,005 A | 11/1993 | Eriksson et al. |
| 5,300,054 A | 4/1994 | Feist et al. |
| 5,304,161 A | 4/1994 | Noel et al. |
| 5,324,575 A | 6/1994 | Sultze et al. |
| 5,346,485 A | 9/1994 | Yarbrough et al. |
| 5,348,547 A | 9/1994 | Payne et al. |
| 5,364,382 A | 11/1994 | Latimer et al. |
| 5,368,926 A | 11/1994 | Thompson et al. |
| 5,387,208 A | 2/1995 | Ashton et al. |
| 5,419,956 A | 5/1995 | Roe |
| 5,422,169 A | 6/1995 | Roe |
| 5,429,629 A | 7/1995 | Latimer et al. |
| 5,429,788 A | 7/1995 | Ribble et al. |
| 5,439,458 A | 8/1995 | Noel et al. |
| 5,460,622 A | 10/1995 | Dragoo et al. |
| 5,482,761 A | 1/1996 | Palumbo et al. |
| 5,486,166 A | 1/1996 | Bishop et al. |
| 5,486,167 A | 1/1996 | Bragoo et al. |
| 5,490,846 A | 2/1996 | Ellis et al. |
| 5,516,569 A | 5/1996 | Veith et al. |
| 5,531,727 A | 7/1996 | Cohen et al. |
| 5,531,728 A | 7/1996 | Lash |
| 5,547,541 A | 8/1996 | Hansen et al. |
| 5,558,655 A | 9/1996 | Jezzi et al. |
| 5,562,645 A | 10/1996 | Tanzer et al. |
| 5,562,646 A | 10/1996 | Goldman et al. |
| 5,569,226 A | 10/1996 | Cohen et al. |
| 5,589,117 A | 12/1996 | Yang |
| 5,599,334 A | 2/1997 | Johnston et al. |
| 5,599,335 A | 2/1997 | Goldman et al. |
| 5,599,336 A | 2/1997 | Plischke |
| 5,601,542 A | 2/1997 | Melius et al. |
| 5,614,147 A | 3/1997 | Pelley |
| 5,614,283 A | 3/1997 | Potnis et al. |
| 5,635,239 A | 6/1997 | Chen et al. |
| 5,641,441 A | 6/1997 | Yang |
| 5,665,082 A | 9/1997 | Boulanger |
| 5,669,894 A | 9/1997 | Goldman et al. |
| 5,681,300 A | 10/1997 | Ahr et al. |
| 5,693,162 A | 12/1997 | Gustafsson et al. |
| 5,695,487 A | 12/1997 | Cohen et al. |
| 5,700,254 A | 12/1997 | McDowall et al. |
| 5,716,703 A | 2/1998 | Payne |
| 5,728,081 A | 3/1998 | Baer et al. |
| 5,728,083 A | 3/1998 | Cohen et al. |
| 5,741,241 A | 4/1998 | Guidotti et al. |
| 5,749,863 A | 5/1998 | Payne |
| 5,752,945 A | 5/1998 | Mosley et al. |
| 5,866,242 A | 2/1999 | Tan et al. |
| 5,916,670 A | 6/1999 | Tan et al. |

PROCESS FOR MAKING A SOFT, STRONG, ABSORBENT MATERIAL FOR USE IN ABSORBENT ARTICLES

CROSS-REFERENCE TO RELATED APPLICATIONS

This application is a continuation-in-part of the U.S. national stage patent application filed Jul. 8, 1999 from the international patent application Serial No. PCT/US98/00639, filed Jan. 15, 1998 and which designates the United States, which is a continuation-in-part application of U.S. patent application Ser. No. 08/948,987 filed Oct. 10, 1997, now U.S. Pat. No. 5,916,670, which itself is a continuation-in-part application of U.S. patent application Ser. No. 08/784,536 filed Jan. 17, 1997, now U.S. Pat. No. 5,866,242. The disclosures of the three patent applications are incorporated herein by reference.

STATEMENT REGARDING FEDERALLY-SPONSORED RESEARCH OR DEVELOPMENT

Not applicable.

REFERENCE TO MICROFICHE APPENDIX

Not applicable.

TECHNICAL FIELD

This invention relates to a process for making absorbent materials to be used as absorbent cores in articles such as disposable diapers, feminine hygiene products and incontinence devices. More particularly, the present invention relates to a process for making improved absorbent materials that are high density, strong, soft materials with superior absorption properties.

BACKGROUND OF THE INVENTION AND TECHNICAL PROBLEMS POSED BY THE ART

Disposable absorbent articles, such as diapers, feminine hygiene products, adult incontinence devices and the like have found widespread acceptance. To function efficiently, such absorbent articles must quickly absorb body fluids, distribute those fluids within and throughout the absorbent article and be capable of retaining those body fluids with sufficient energy to dry the surface when placed under loads. In addition, the absorbent article should be sufficiently soft and flexible so as to comfortably conform to body surfaces and provide close fit for lower leakage.

While the design of individual absorbent articles varies depending upon use, there are certain elements or components common to such articles. The absorbent article contains a liquid pervious top sheet or facing layer, which facing layer is designed to be in contact with a body surface. The facing layer is made of a material that allows for the substantially unimpeded transfer of fluid from the body into the core of the article. The facing layer should not absorb fluid per se and, thus, should remain dry. The article further contains a liquid impervious back sheet or backing layer disposed on the outer surface of the article and which layer is designed to prevent the leakage of fluid out of the article.

Disposed between the facing layer and backing layer is an absorbent member referred to in the art as an absorbent core or panel. The function of the absorbent core is to absorb and retain body fluids entering the absorbent article through the facing layer. Because the origin of body fluids is often localized, it is desirable to provide means for distributing fluid throughout the dimensions of the absorbent core to make full use of all the available absorbent material. This is typically accomplished either by providing a distribution member disposed between the facing layer and absorbent core and/or altering the composition of the absorbent core per se.

Fluid can be distributed to different portions of the absorbent core by means of a transition layer, transfer layer, or acquisition layer disposed between the facing layer and core. Because of the proximity of such an acquisition layer to the body surface of the wearer, the acquisition layer should not be formed from material that retains large amounts of fluid. The purpose of the acquisition layer is to facilitate lateral spreading of the fluid, and further to rapidly transfer and distribute the fluid to the absorbent core.

The absorbent core is typically formulated of a cellulosic wood pulp fiber matrix, which is capable of absorbing large quantities of fluid. Absorbent cores can be designed in a variety of ways to enhance fluid absorption and retention properties. By way of example, the fluid retention characteristics of absorbent cores can be greatly enhanced by disposing superabsorbent materials in amongst fibers of the wood pulp. Superabsorbent materials are well known in the art as substantially water-insoluble, absorbent polymeric compositions that are capable of absorbing large amounts of fluid in relation to their weight and forming hydrogels upon such absorption. Absorbent articles containing blends or mixtures of pulp and superabsorbents are known in the art.

The distribution of superabsorbents within an absorbent core can be uniform or non-uniform. By way of example, that portion of an absorbent core proximate to the backing layer (farthest away from the wearer) can be formulated to contain higher levels of superabsorbent than those portions of the core proximate the facing or acquisition layer. By way of further example, that portion of the core closest to the site of fluid entry (e.g., acquisition zone) can be formulated to transport (wick) fluid into surrounding portions of the core (e.g., storage zone).

In addition to blending pulp with superabsorbent material, a variety of other means for improving the characteristics of pulp have been described. For example, pulp boards can be more easily defiberized by using chemical debonding agents (see, e.g., U.S. Pat. No. 3,930,933). In addition, cellulose fibers of wood pulp can be flash-dried prior to incorporation into a composite web absorbent material (see, e.g., U.K. Patent Application GB 2272916A published on Jun. 1, 1994). Still further, the individualized cellulosic fibers of wood pulp can be cross-linked (see, e.g., U.S. Pat. Nos. 4,822,453; 4,888,093; 5,190,563; and 5,252,275). All of these expedients have the disadvantage of requiring the wood pulp manufacturer to perform time-intensive, expensive procedures during the wood pulp preparation steps. Thus, use of these steps results in substantial increases in the cost of wood pulp.

Although all of the above-described treatment steps have been reported to improve the absorption characteristics of pulp for use as absorbent cores, there are certain disadvantages associated with such treatments. By way of example, the manufacturer of the end use absorbent article (e.g. feminine hygiene product or diaper) must fluff the fibers in the wood pulp so as to detach the individual fibers bound in that pulp. Typically, pulp has a low moisture content, and this causes the individual fibers to be relatively brittle—resulting in fine dust due to fiber breakage during fluffing operations. If the pulp manufacturer performs such fluffing prior to shipment to the absorbent article maker, the transportation costs of the pulp are increased. At least one pulp manufacturer has attempted to solve this problem by producing flash-dried pulp without chemical bonding agents in a narrow range of basis weights and pulp density (see U.S. Pat. No. 5,262,005). However, even with this process, the manufacturer of the absorbent article must still process the pulp after purchase.

There have been numerous attempts by the manufacturers of absorbent materials to produce highly absorbent, strong, soft core materials. U.S. Pat. No. 4,610,678 discloses an air-laid material containing hydrophilic fibers and superabsorbent material, wherein the material is air-laid in a dry state and compacted without the use of any added binding agents. Such material, however, has low integrity and suffers from shake-out or loss of substantial amounts of superabsorbent material. U.S. Pat. No. 5,516,569 discloses that superabsorbent material shake-out can be reduced in air-laid absorbents by adding significant amounts of water to material during the air-laying process. The resultant material, however, is stiff, of low density and has a high water content (greater than about 15 weight percent). U.S. Pat. No. 5,547,541 discloses that high density air-laid materials containing hydrophilic fibers and superabsorbent material can be made by adding densifying agents to the material. The use of such agents; however, increases the production cost of the material.

U.S. Pat. No. 5,562,645 discloses low density absorbent materials (density less than 0.25 g/cc). The use of such low density, bulky materials increases the cost of transportation and handling. U.S. Pat. No. 5,635,239 discloses an absorbent material that contains two complex forming agents that interact when wetted to form a complex. The complex forming agents are polymeric olefins. European Patent Application No. EP 0763364 A2 discloses absorbent material that contains cationic and anionic binders that serve to hold the superabsorbent material within the material. The use of such agents and binders increases the cost of making the absorbent material and poses a potential environmental hazard.

The U.S. Pat. Nos. 2,955,641 and 5,693,162 disclose (1) the application of steam to absorbent material to increase the moisture content of the absorbent material, and (2) compressing the absorbent material. The U.S. Pat. No. 5,692,162 also discloses the use of hot calendering rolls (which may be patterned) to form a densified structure, and the use of thermoplastic and thermo-setting resins suitable for thermal bonding.

Nevertheless, there continues to be a need in the art for an improved process for making an absorbent material which satisfies the absorbency, strength and softness requirements needed for use as an absorbent core in disposable absorbent articles and which also provides time and cost savings to both the pulp manufacturer and the manufacturer of the absorbent article.

BRIEF SUMMARY OF THE INVENTION

According to one aspect of the present invention, a process is provided for making an absorbent material free of added chemical binders and heat set bonding agents. A web is formed with at least one layer of a mixture of cellulosic fibers and superabsorbent material. The moisture content of the web is increased so as to increase the web density. Then, the web is compacted at an elevated temperature to further increase the web density and to effect hydrogen bonding within the web.

In a preferred form of the process of the invention, the web moisture content is increased by conveying the web through a region of steam having a temperature above about 100° C., and the web is compacted between calendering rolls wherein at least one of the rolls is heated to a surface temperature in the range of between about 70° C. and about 180° C.

The process of the present invention can be used to make various forms of absorbent material. One form of the absorbent material has a basis weight of from about 180 g/cm$^2$ to about 600 g/cm$^2$, a density of from about 0.30 g/cc to about 0.45 g/cc. The material is air-laid as a bottom layer of pulp, a middle layer of pulp and superabsorbent material disposed in amongst the pulp, and a top acquisition layer of pulp. The pulp preferably has a Kappa value of less than about 100. The absorbent material includes from about 40 weight percent to about 90 weight percent cellulosic fibers and from about 10 weight percent to about 60 weight percent superabsorbent material. Such absorbent material has a water content of less than about 10 weight percent, and a density of greater than about 0.25 g/cc.

In another form, the absorbent material includes from about 40 weight percent to about 90 weight percent cellulosic fibers and from about 10 weight percent to about 60 weight percent superabsorbent material. Such absorbent material has a water content of about 10 weight percent or less, and a density of greater than about 0.25 g/cc.

With all forms of the material, it is preferred that at least some of the cellulosic fibers have a relative crystallinity of less than about 65 percent.

In another form, the absorbent material has a basis weight of from about 100 g/m$^2$ to about 500 g/m$^2$ and a density of from about 0.25 g/cc to about 0.50 g/cc. Such material includes a core of cellulosic fibers obtained from pulp wherein at least some of the pulp fibers have a Kappa value of less than about 100. A carrier layer (e.g., a layer of tissue) may be superimposed on an outer surface of the core. The carrier layer is preferably crepe tissue. At least some of the cellulosic fibers have a relative crystallinity of less than about 65 percent. The core contains from about 40 weight percent to about 100 weight percent cellulosic fibers and from about 0 weight percent to about 60 weight percent superabsorbent material. Preferably, the core contains from about 40 weight percent to about 90 weight percent cellulosic fibers and from about 10 weight percent to about 60 weight percent superabsorbent material.

In another form, the absorbent material has a density of from about 0.25 g/cc to about 0.5 g/cc, and a basis weight of from about 200 g/m$^2$ to about 500 g/m$^2$. Such material consists essentially of (1) from about 60 weight percent to about 90 weight percent cellulosic fibers at least some of which fibers are obtained from pulp having a Kappa value of less than about 100, wherein at least some of the cellulosic fibers have a relative crystallinity of less than about 60 percent; (2) from about 10 weight percent to about 40 weight percent superabsorbent material; and (3) a layer of tissue comprising from about 3 weight percent to about 20 weight percent of the absorbent material. The tissue is preferably crepe tissue.

Preferably, the material is made using cellulosic fibers having a relative crystallinity of preferably less than about 60 percent. More preferably, the cellulosic fibers have a relative crystallinity of less than about 50 percent and, even more preferably a relative crystallinity of less than about 40 percent. At least some of the cellulosic fibers are obtained from pulp having a Kappa value of less than about 75, 50, 25 or 10. More preferably, the Kappa value is less than 5 or 2.5.

In one form of the absorbent material, at least some of the cellulosic fibers in the material are made by a process that includes the step of treating a liquid suspension of pulp at a temperature of from about 15° C. to about 60° C. with an aqueous alkali metal salt solution having an alkali metal salt concentration of from about 2 weight percent to about 25 weight percent of said solution for a period of time ranging from about 5 minutes to about 60 minutes.

In another form of the absorbent material, at least some of the cellulosic fibers have been flash dried.

In another form of the absorbent material, the cellulosic fibers are not flash dried, but are processed through a hammer mill.

An especially preferred form of absorbent material made by the process of this invention has a density of from about 0.35 g/cc to about 0.45 g/cc, and a basis weight of from about 200 g/m$^2$ to about 500 g/m$^2$.

Preferred forms of the material have superior absorptive properties. The absorbent material made by the process of this invention can be used to make absorbent articles, such as a diaper, a feminine hygiene product, or an incontinence device.

BRIEF DESCRIPTION OF THE DRAWINGS

In the drawings, which form a portion of the specification.

DETAILED DESCRIPTION

Figure 1:
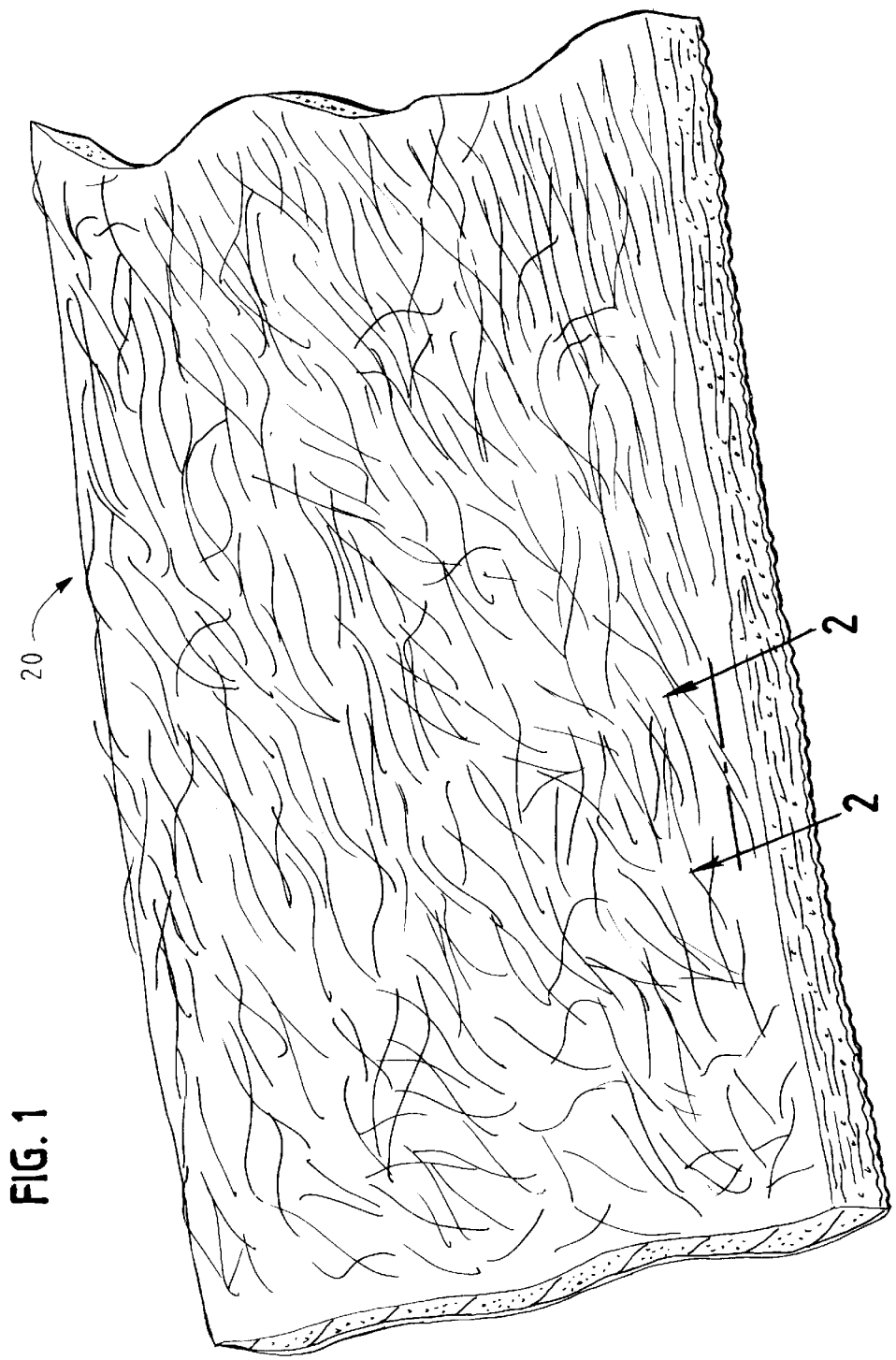
FIG. 1 is a simplified, fragmentary, perspective view of a sheet of absorbent material which can be made by the process of the present invention.

The process of the present invention provides an improved absorbent material that is particularly well-suited for use as cores in absorbent articles such as diapers, feminine hygiene products, incontinence devices, and the like. The absorbent material can also be used as an absorbent core in any device used to absorb body exudates (e.g., urine, breast milk, blood, serum). Thus, the absorbent material can be incorporated into breast pads for nursing mothers or used as absorbent material in surgical drapes (e.g., towels) or wound dressings.

The preferred form of the absorbent material includes a blend or mixture of cellulosic fibers and superabsorbent disposed in and amongst fibers of that pulp. The absorbent material has a unique combination of suppleness, strength, and absorbency characteristics that makes it particularly suitable for use in absorbent articles. The absorbent material can be used directly by a manufacturer of the absorbent article without the need for any additional processing by that manufacturer other than cutting or folding the absorbent material to the desired size and shape for the absorbent article.

The process of the present invention can be used to make an absorbent material that is soft, that is thin, and that has relatively high density. Additionally, the material can have enhanced absorption properties, and firmly entraps superabsorbent material in the fiber network without the use of chemicals, binders, adhesives, thermoplastic resins, thermoplastic binder fibers, complex forming materials, or the like. The absorbent material has enough integrity (strength) to be processed on conventional disposable product manufacturing equipment without significant fiber breakage.

In one aspect, the process of the present invention can provide an absorbent material that contains from about 40 weight percent to about 100 weight percent cellulosic fibers, from about 0 weight percent to about 60 weight percent superabsorbent material, and about 10 weight percent or less water. As used herein, the phrase "weight percent" means weight of substance per weight of final material as determined under ambient conditions. By way of example, 10 weight percent superabsorbent material means 10 g/m$^2$ superabsorbent material per 100 g/m$^2$ basis weight of the absorbent material.

Cellulosic fibers that can be used in the process of the present invention are well known in the art and include wood pulp, cotton, flax, and peat moss. Wood pulp is preferred. Pulps can be obtained from mechanical or chemi-mechanical, sulfite, kraft, pulping reject materials, organic solvent pulps, etc. Both softwood and hardwood species are useful. Softwood pulps are preferred. It is not necessary to treat cellulosic fibers with chemical debonding agents, cross-linking agents and the like for use in the absorbent material.

As discussed above, a preferred cellulosic fiber for use in the present material is wood pulp. Wood pulp prepared using a process that reduces the lignin content of the wood is preferred. Preferably, the lignin content of the pulp is less than about 16 percent. More preferably, the lignin content is less than about 10 percent. Even more preferably, the lignin content is less than about 5 percent. Most preferably, the lignin content is less than about 1 percent. As is well known in the art, lignin content is calculated from the Kappa value of the pulp. The Kappa value is determined using a standard, well known test procedure (TAPPI Test 265-cm 85). The Kappa value of a variety of pulps was measured and the lignin content calculated using the TAPPI Test 265-cm 85. Peat moss was found to have a Kappa value of about 104 and a lignin content of about 13.5 percent. CTMP pulp was found to have a Kappa value of about 123 and a lignin content of about 16 percent. Pulp prepared from softwood using either the kraft or sulfite methods had a Kappa value of about 1.1 and a lignin content of about 0.15 percent, When that latter pulp was treated using a cold caustic extraction method, the Kappa value was found to be about 0.97 and the lignin content about 0.12 percent.

For use in the process of the present invention, cellulosic fibers are preferably obtained from wood pulp having a Kappa value of less than about 100. Even more preferably, the Kappa value is less than about 75, 50, 25 or 10. Most preferably, the Kappa value is less than about 2.5.

There are certain other characteristics of wood pulp that make it particularly suitable for use in an absorbent material. Cellulose in most wood pulps has a high relative crystallinity (greater than about 65 percent). In a present material, the use of wood pulp with a relative crystallinity of less than about 65 percent is preferred. More preferably, the relative crystallinity is less than about 50 percent. Most preferably, the relative crystallinity is less than about 40 percent. Also, pulps having an increase fiber curl value are preferred.

Means for treating pulps so as to optimize these characteristics are well known in the art. By way of example, treating wood pulp with liquid ammonia is known to decrease relative crystallinity and to increase the fiber curl value. Flash drying is known to increase the fiber curl value of pulp and to decrease crystallinity. Cold caustic treatment of pulp also increases fiber curl and decreases relative crystallinity. Chemical cross-linking is known to decrease relative crystallinity. It is preferred that the cellulosic fibers used to make the absorbent material by the process of this invention are obtained at least in part using cold caustic treatment or flash drying.

A description of the cold caustic extraction process can be found in commonly owned U.S. patent application Ser. No. 08/370,571, filed on Jan. 18, 1995, which application is a continuation-in-part application of U.S. patent application Ser. No. 08/184,377, filed on Jan. 21, 1994, now abandoned. The disclosures of these two U.S. patent applications are incorporated in their entirety herein by reference thereto.

Briefly, a caustic treatment is typically carried out at a temperature less than about 60° C., but preferably at a temperature less than 50° C., and more preferably at a temperature between about 10° C. and about 40° C. A preferred alkali metal salt solution is a sodium hydroxide solution newly made up or as a solution by-product in a pulp or paper mill operation, e.g., hemicaustic white liquor, oxidized white liquor and the like. Other alkali metals such as ammonium hydroxide and potassium hydroxide and the like can be employed. However, from a cost standpoint, the preferable salt is sodium hydroxide. The concentration of alkali metal salts is typically in a range from about 2 to about 25 weight percent of the solution, and preferably from about 6 to about 18 weight percent. Pulps for high rate, fast absorbing applications are preferably treated with alkali metal salt concentrations from about 10 to about 18 weight percent.

As is well known in the art, flash drying is a method for drying pulp in which pulp is partially dewatered, fiberized, and fed into a stream of hot air which causes the moisture contained in the pulp to be flashed off. Briefly, the pulp, initially at a consistency of 30–45% (containing 55–70% water), is conveyed directly into a fluffer (e.g., a disk refiner) where mechanical action is used to fiberize (break up and separate) and disperse the fibers for the flash drying system. Once discharged from the fluffer device, the fiberized pulp is fed into a flash drying system. The drying system itself is made up of two stages, each of which consists of two drying towers. The fiber is conveyed through the drying towers by high velocities of hot air. The inlet air temperature for the first stage is approximately 240–260° C. while the inlet air temperature for the second stage is approximately 100–120° C. Following each drying stage, the pulp and hot air are then conveyed into a cyclone separator, where the hot air, now containing moisture evaporated from the pulp, is exhausted vertically. Exhaust temperatures for the first stage, in this case, are approximately 100–120° C., and the exhaust temperatures for the second stage are approximately 90–100° C. At the same time, a material-handling fan draws the pulp fibers through the cyclone cone and on to the next part of the system. Finally, following the second stage cyclone separator, the dried pulp is passed through a cooling stage consisting of a cooling fan which conveys ambient air, and is then passed through a final cooling cyclone separator. The residence time for the entire system, including both drying stages, cyclone separation, and cooling, is approximately 30–60 seconds at the feed rate used (1.5 kg of dry material per minute).

A downside to producing flash dried fiber using the type of system described above is the production of localized fiber bundles in the final product. Fiber bundles are formed during the fiberization of the pulp by mechanical action within the fluffer device. The system above uses a disk refiner consisting of two grooved, circular plates at a set gap width, in this case 4 mm. One plate is in a fixed position while the other plate is rotated at high speeds. The pulp is fed into the gap between the two plates and the rotation of the plate results in the separation of fibers along the grooves. Unfortunately, as the pulp is fiberized, some of the individual fibers tend to become entangled with one another, forming small bundles consisting of several individual fibers. As these entangled fibers are flash dried and the moisture is removed, the entanglements tighten and harden to form small localized fiber bundles throughout the flash dried pulp. The presence of large numbers of these localized fiber bundles within the final airlaid products produced using the flash dried pulp can have a deleterious effect on the product physical characteristics and performance. The number of localized fiber bundles can be substantially reduced by using cold caustic extracted pulp.

According to one aspect of the process of the present invention (as described hereinafter), an absorbent material is manufactured to contain a superabsorbent material. Superabsorbent materials are well known in the art. As used herein, the term "superabsorbent material" means a substantially water-insoluble polymeric material capable of absorbing large quantities of fluid in relation to their weight. The superabsorbent material can be in the form of particulate matter, flakes, fibers and the like. Exemplary particulate forms include granules, pulverized particles, spheres, aggregates and agglomerates. Exemplary and preferred superabsorbent materials include salts of crosslinked polyacrylic acid such as sodium polyacrylate. Superabsorbent materials are commercially available (e.g., from Stockhausen GmbH, Krefeld, Germany). A preferred form of the absorbent material contains from about 0 to about 60 weight percent superabsorbent material and, more preferably from about 20 to about 60 weight percent superabsorbent material. Such a preferred form of absorbent material has about 40 to about 100 weight percent cellulosic fibers and, more preferably from about 60 to about 80 weight percent cellulosic fibers.

According to yet another aspect of the present invention, a unique process is provided for manufacturing a web of absorbent material, but the process may be implemented without including a superabsorbent material in all parts of the web or even in any part of the web.

The absorbent material made by the process of the present invention preferably has a moisture content of about 10% or less to discourage bacterial growth. Also, the material is free of added chemical binders and heat set bonding agents.

FIG. 1 illustrates one form of an absorbent material that can be made by the process of the present invention. The absorbent material is designated in FIG. 1 generally by the reference number 20. The material 20 is typically made by the process of the present invention in a relatively wide sheet that can be provided in sheet form or in a large roll to a manufacturer of absorbent articles. A typical thickness of the material is between 0.5 mm and 2.5 mm. It is presently contemplated that most absorbent article manufacturers would use the material 20 with a thickness of about 2.00 mm.

Figure 2:
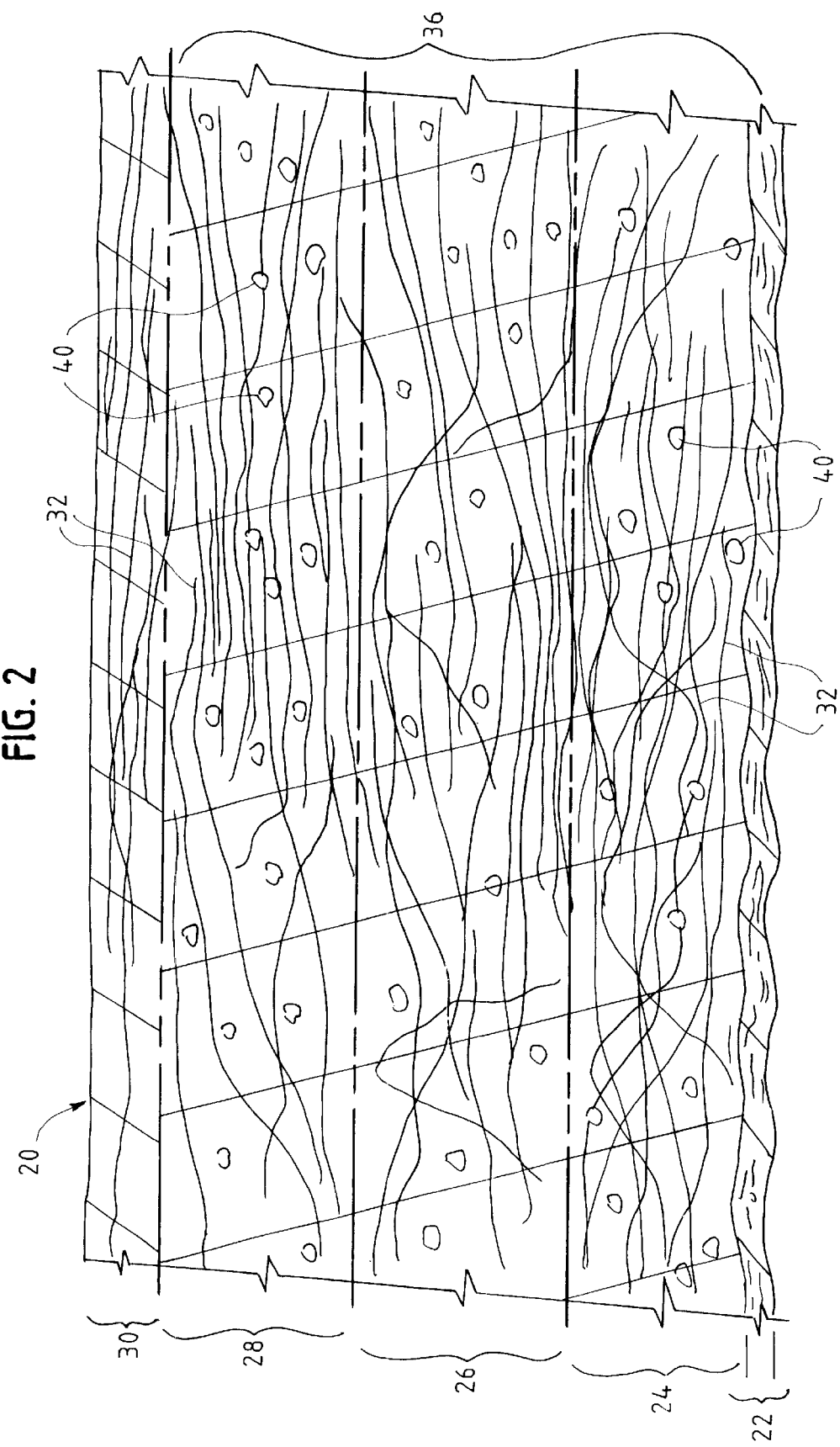
FIG. 2 is a greatly enlarged, fragmentary, cross-sectional view taken generally along the plane 2—2 in FIG. 1, and in FIG. 2 the height or thickness of portions of the illustrated structure have been exaggerated for ease of illustration, and it should be understood that FIG. 2 is not necessarily drawn to scale with respect to the thicknesses of the various portions.

FIG. 2 illustrates a cross section of the material. Regions of various thickness in the material 20 illustrated in FIG. 2 are not necessarily to scale and may in some respects be exaggerated for purposes of clarity and ease of illustration.

The absorbent material 20 illustrated in FIG. 2 includes an optional carrier layer 22. The carrier layer 22 may be, for example, a spunbond, melt blown non-woven consisting of natural or synthetic fibers. Another, and preferably preferred, material that could be used for the carrier layer is tissue.

Suitable tissue materials for use as a carrier layer in absorbent products are well known to those of ordinary skill in the art. Preferably such tissue is made of bleached wood pulp and has an air permeability of about 273–300 CFM (cubic feet minute). The tensile strength of the tissue is such that it retains integrity during formation and calendering of the absorbent material. Suitable MD (machine direction) and CD (cross direction) tensile strengths, expressed in newtons/meter, are about 100–130 and 40–60, respectively. Tissue for use in air-laying absorbent materials are commercially available (e.g., from Duni AB, Sweden). In a preferred embodiment, the tissue is crepe tissue having a sufficient number of crepes per inch to allow a machine direction elongation of between 15 and 30 percent (as determined by the SCAN P44:81 test method).

The absorbent material 20 above the tissue layer 22 typically includes one or more different strata or layers. The thickness of each layer, and the number of layers, may vary. FIG. 2 illustrates a presently contemplated commercial form of the material for a particular application in feminine hygiene products. The absorbent material 20 illustrated in FIG. 2 includes a bottommost or first layer 24, a second layer 26, a third layer 28, and a fourth layer or top layer 30. In the form of the absorbent material 20 illustrated in FIG. 2, the layers 24, 26, and 28 together define an absorbent core portion 36. The top layer 30, which is optional, is typically characterized as a transition layer, acquisition layer, or transfer layer described in detail hereinafter.

The layers 24, 26, 28, and 30 are referred to as layers or strata because the material forming such layers or strata is initially laid down in the process of the present invention as separate strata or layers one on top of the other as explained in detail hereinafter. However, after completion of the process of making the absorbent material, the layers or strata are part of a unitary or integral structure. Typically, there is little discernable visual difference between the different layers. If one tries to separate the absorbent material into the layers or strata by which it was initially laid down in the manufacturing process, it will be found that the finished absorbent material does not readily pull apart or delaminate into specifically identifiable layers or strata corresponding to the layers or strata laid down during the production process.

Preferably, when a carrier layer, such as tissue layer 22, is used, the tissue layer 22 is lightly embedded into the bottom layer 24 of the absorbent pore portion 36, and this can be effected during processing with a knurled (or other embossed) calendering roll as described in more detail hereinafter. Preferably, if a knurled calendering roll is used, the knurled surface of the roll has a depth greater than 5% of the thickness of the carrier layer (tissue layer).

Typically, an absorbent article manufacturer would add a facing layer, top sheet, or cover stock (not illustrated) over the transition layer 30, and such a facing layer contacts the skin of the person wearing the article. The top, transition layer 30 functions as an acquisition layer to receive liquid (e.g., menses or urine) in the first moments of discharge through the facing layer. This transition layer 30 picks up the liquid from the absorbent article facing layer very quickly and distributes the liquid to the absorbent core 36. The transition layer 30 maintains a distance between the facing layer and the core 36 to inhibit liquid from travelling back from the core 36 to the skin of the wearer of the absorbent article. The transition layer 30 facilitates the lateral spreading of the liquid, especially during second and subsequent discharges of liquid into the absorbent article. In an alternate embodiment, the transition layer 30 may be omitted.

The layers 24, 26, and 28 include pulp fibers 32 which have a typical average length of about 2.40 mm. Preferably, at least some of the pulp fibers 32 are produced by the above-discussed cold caustic extraction process. This includes treating a liquid suspension of pulp containing cellulosic fibers at a temperature of from about 15° C. to about 60° C. with an aqueous alkali metal salt solution having an alkali metal salt concentration from about 2 weight percent to about 25 weight percent of the solution for a period of time ranging from about 5 minutes to about 60 minutes. The treated pulp cellulosic fibers are then either flash-dried or processed through a hammermill.

The absorbent core portion layers 24, 26, and 28 each preferably include a superabsorbent material of the type previously described and which preferably is provided in the form of superabsorbent granules or particles 40. The top, transition layer 30 is free of superabsorbent particles. If the transition layer 30 is omitted, then the top layer of the remaining absorbent core portion layers (e.g., absorbent core portion top layer 28) would preferably be free of superabsorbent particles.

In a preferred form of the absorbent material 20 which is illustrated in FIG. 2 and which has a transition layer 30, each of the absorbent core portion 36 layers 24, 26, and 28 includes superabsorbent particles. If desired, the layers containing pulp and superabsorbent can be laid down as a homogeneous blend or as a heterogeneous blend wherein the level of superabsorbent varies with proximity to the bottom (i.e., the bottom carrier layer 22). In modified forms of the absorbent materials, the concentration (weight percent) of superabsorbent material in each layer 24, 26, and 28 can vary, as can the nature or type of the particular superabsorbent material. Also, the superabsorbent material could be limited to only one or some of the layers that constitute the absorbent core pore portion 36.

Preferably, the total basis weight of the pulp and superabsorbent material in the bottom layer 24 is typically between about 50 and about 270 g/m$^2$. The total basis weight of the layer 26 is typically between about 50 and about 270 g/m$^2$. The total basis weight of the layer 28 is typically between about 50 and about 270 g/m$^2$. The total basis weight of the top layer 30 would typically be between about 0 and about 50 g/m$^2$.

The preferred thickness of the top, transition layer 30 is in the range of between about 0.20 mm and about 0.50 mm. The preferred thickness of each of the core layers 24, 26, and 28 is in the range of between about 0.5 mm and about 0.9 mm.

The average density of the absorbent material 20 preferably ranges between 0.25 and 0.4 g/cm$^3$. The moisture content of the absorbent material 20 is preferably less than about 10%, is more preferably less than about 7%, and preferably lies in the range of between about 5% and about 6%.

Figure 3:
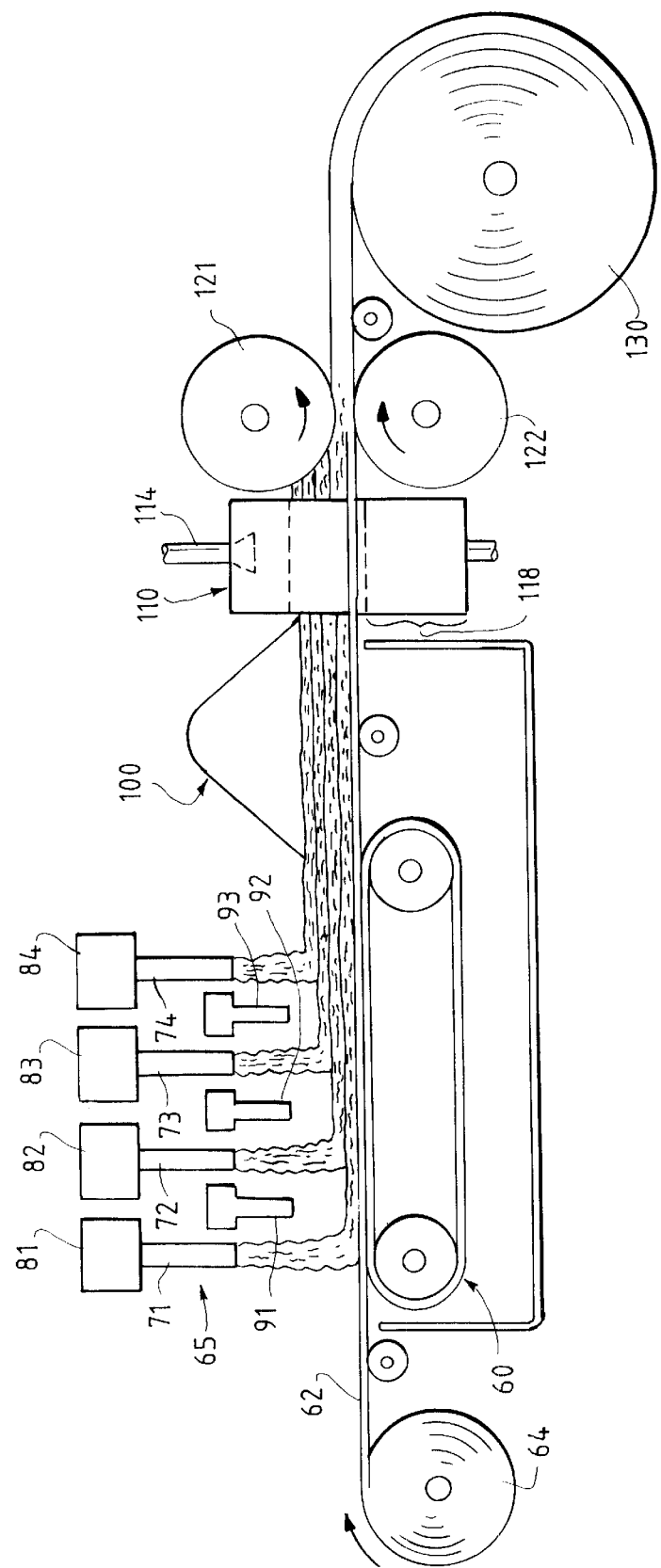
FIG. 3 is a diagrammatic view illustrating one form of the process of the present invention.

The above-described absorbent materials may be made with the process of the present invention. One form of the process of the present invention is diagrammatically illustrated in FIG. 3. The illustrated process employs an endless wire, screen, or belt 60 on which the absorbent material components are deposited.

The process permits the optional incorporation of a carrier layer in the absorbent material (e.g., tissue layer 22 in the absorbent material 20 described above with reference to FIG. 2). To this end, a tissue web 62 is unwound from a tissue web roll 64 and directed over the endless screen 60. A series of forming heads 64 is provided over the endless screen 60. In the preferred form of the process, the series includes a first forming head 71, a second forming head 72, a third forming head 73, and a fourth forming head 74. A lesser or greater number of forming heads may be provided depending upon how many layers of material are to be laid down.

Cellulosic fibers, in the form of the above-described cold caustic extracted pulp fibers, are processed using a conventional hammermill (not illustrated) to individualize the fibers. The individualized fibers are blended with superabsorbent material, granules, or particles in a separate blending system supplying each forming head. The forming head 71 is connected with a blending system 81, the forming head 72 is connected with a blending system 82, and the forming head 73 is connected with a blending system 83. The pulp fibers and superabsorbent granules or particles are blended and conveyed pneumatically into the forming heads. Chemical binding agents and heat set bonding agents are not added during fiber processing or during the blending of the fibers with the superabsorbent material.

The forming head 74 is connected with a blending system 84, and the forming head 74 provides the pulp fibers or other components for the top, transition layer 30. The top layer 30 has no superabsorbent material as previously explained with reference to the absorbent material 20 illustrated in FIG. 2.

The blending and distribution of the materials can be controlled separately for each forming head. Controlled air circulation and winged agitators in each blending system produce a substantially uniform mixture and distribution (of the pulp and superabsorbent particles for blending systems 81, 82, and 83 and of the pulp fibers alone for blending system 84).

The superabsorbent particles can be either thoroughly and homogeneously blended throughout the absorbent core portion of the structure being produced, or contained only in a specific layer or layers by distributing the superabsorbent particles to selected forming heads.

If desired, the superabsorbent particles can be separately discharged from separate forming heads 91, 92, and 93 as individual layers of 100% superabsorbent. In such an optional configuration, the superabsorbent particle forming head 91 is located between the forming heads 71 and 72, the superabsorbent particle forming head 92 is located between the forming heads 72 and 73, and the superabsorbent particle forming head 93 is located between the forming heads 73 and 74. If the separate superabsorbent particle forming heads 91, 92, 93 are employed, then additional superabsorbent particles could also still be blended in the blending systems 81, 82, and 83. Alternatively, only pulp fibers exclusively could be conveyed to and through the blending systems 81, 82, and 83 and the forming heads 71, 72, and 73, respectively, when superabsorbent material is discharged from the forming head 91, 92, and 93.

The material from each forming head is deposited by vacuum onto the tissue web or carrier layer 62 (or directly onto the endless screen 60) to form a layered, absorbent web. The layered, absorbent web is conveyed with the help of a conventional vacuum transfer device 100 from the end of the endless screen 60 to a moisture addition apparatus 110.

The apparatus 110 typically includes a housing or enclosure and suitable means for supplying moisture and/or controlling the moisture in the enclosure around the layered web. In one contemplated embodiment, the moisture is supplied in the form of low pressure steam through a nozzle 114. On the side of the web opposite the nozzle 114, the apparatus may include a steam suction chamber 118. Other means may be provided in the device 110 for establishing a desired atmosphere around the layered web wherein the moisture content of the atmosphere is controlled.

In the presently contemplated preferred embodiment of the process of the present invention, the moisture is provided to the device 110 in the form of steam at a pressure of between about 0 psi and about 20 psi. and at a temperature of between about 100° C. and about 125° C. The steam is preferably maintained on one side of the web at a temperature of at least about 100° C. The steam flows into and through the layered web and increases the moisture content of the web. According to a preferred form of the process of the present invention, the moisture content of the web is increased to about 10 weight percent or less, preferably to about 9 weight percent. There is no thermal bonding of the pulp fibers. However, it is also presently believed that the addition of the moisture increases the density of the web and facilitates the establishment of hydrogen bonding of the pulp fibers to each other, as well as of the tissue layer to the pulp fibers, and this increases the strength or integrity of the finished absorbent material.

As the moisturized, layered web exits the moisture addition device 110, it is compressed or compacted between a pair of heated, calendering rolls-upper roll 121 and lower roll 122. This increases the density of the web. In the preferred form where the top layer is free of superabsorbent material, the superabsorbent material in the underlying portion of the web does not contact, and stick to, the heated, upper calendering roll.

The upper roll 121 is typically a steel roll, and the lower roll 122 is typically a flexroll having a hardness of about 85 SH D. Although both rolls could be smooth, in the preferred process, the upper roll 121 has a smooth surface, and the lower roll 122 has a knurled surface. The knurled surface functions to embed the tissue layer 62, or other type of carrier layer, into the bottom of the absorbent material. Preferably, the knurled surface has a depth greater than 5% of the thickness of the carrier layer.

Each roll 121 and 122 is heated to a temperature of between about 70° C. and about 180° C., preferably about 80° C. The weight of the upper roll 121 bears on the layered web. Additional force may be provided with conventional hydraulic actuators (not illustrated) acting on the axle of the roll 121. In one form of the invention, the web is compacted between the rolls 121 and 122 under a load of between about 50 and about 400 newtons per millimeter of transverse web width. It is presently believed that the heated compaction increases the density of the web and effects the establishment of hydrogen bonding of the pulp fibers to each other, as well as of the tissue layer-to the pulp fibers, so as to increase the strength and integrity of the finished absorbent material. This provides a finished product with exceptional resistance to shake-out of superabsorbent material.

The compressed and densified web is wound into a roll 130 using conventional winding equipment.

The processing line is preferably run at a line speed of about 0.5 meters per second to about 5.0 meters per second. The residence time of the web within the moisture addition device 110 is preferably between about 0.1 and about 1.0 seconds.

The presently contemplated preferred form of the process of the present invention employs calendering rolls 121 and 122 to apply heat and pressure to the web. It will be appreciated, however, that the present invention also contemplates use of other means for compacting and applying heat to the web. For example, a pair of moving, heated platens may be employed in place of the calendering rolls. Alternatively, opposed, heated, endless belt assemblies may be employed to compact and heat the web in place of the calendering rolls. Finally, the instrumentalities for compacting or densifying the web may be separated from the instrumentalities for applying heat to the web. However, it presently appears to be most practical to combine such instrumentalities, as with heated calendering rolls.

A single layer or multilayer absorbent material made by the process of the present invention is of relatively high density and has a composite density that is preferably greater than about 0.25 g/cc. In preferred embodiments, the absorbent material has a composite density in the range of from about 0.25 g/cc to about 0.50 g/cc. More preferably, the density is from about 0.30 g/cc to about 0.45 g/cc. Most preferably, the density is from about 0.35 g/cc to about 0.45 g/cc.

A high density absorbent material made by the process of the present invention that contains superabsorbent material is surprisingly and unexpectedly supple. The term "supple" is used herein to describe these characteristics of softness, flexibility and bendability. A related characteristic is Gurley stiffness which measures the stiffness of absorbent materials. The greater the value of Gurley stiffness, the more rigid and inflexible the material. The inverse of Gurley stiffness, expressed as inverse grams ($g^{-1}$), is thus a measure of the softness, bendability and flexibility of absorbent materials. Suppleness is defined and expressed as the inverse of Gurley stiffness and has the units $g^{-1}$.

The high density absorbent material is strong notwithstanding its suppleness. Pad integrity is a well known characterization of absorbent material strength. The high density absorbent material made by the process of the present invention has good strength (high pad integrity).

An absorbent material can be prepared by the process of the present invention over a wide range of basis weights without adversely affecting its softness or strength. Thus, the absorbent material can have a basis weight in the range of from about 50 g/m² to about 800 g/m² and greater. In a preferred form, the basis weight ranges from about 100 g/m² to about 500 g/m² and, more preferably from about 100 g/m² to about 250 g/m² or from about 350 g/m² to about 450 g/m².

The process of the present invention can be used to make an absorbent material which has superior absorptive properties when compared to existing materials. The absorptive properties of materials can be evaluated in a variety of ways. Of particular relevance to manufacturers of absorbent articles is the ability of the material to absorb large quantities of fluid against a load and to distribute that fluid away from the point of fluid deposition or entry.

Wicking is the ability of an absorbent material to direct fluid away from the point of fluid entry and distribute that fluid throughout the material. An absorbent material made by the process of this invention has good wicking properties.

The unique combination of strength, absorptive capability and suppleness of absorbent material which can be made by the process of the present invention has significant advantages to a manufacturer of absorbent articles. Typically, such a manufacturer purchases pulp, and then processes that pulp on-line in a manufacturing plant as the final article (e.g., diaper, sanitary napkin) is being made. Such processing steps may include defibering of the pulp, adding superabsorbent and the like. In an on-line system, the rapidity with which such steps can be carried out is limited by the slowest of the various steps. An example of a pulp that requires such processing steps (e.g., defibering) is disclosed in U.S. Pat. No. 5,262,005.

The need of the manufacturer to defiberize or otherwise process existing materials on-line means that the overall production process is substantially more complex. Further, the manufacturer must purchase, maintain, and operate the equipment needed to carry out such processing steps. The overall production cost is thus increased.

An absorbent material of the type produced by the process of the present invention can be directly incorporated into a desired absorbent article without the need for such processing steps. The manufacturer of the absorbent article does not have to defiber or otherwise treat the absorbent material made by the process of the present invention in any way other than shaping the absorbent material into the desired shape. In this way, the manufacturer can speed up the assembly process and realize substantial savings in cost and time.

The process of the present invention can be employed to make an absorbent material which also has a good capability to retain superabsorbent material when subjected to mechanical stress.

Forms of Absorbent Material for Use in Feminine Hygiene Products

Figure 4:
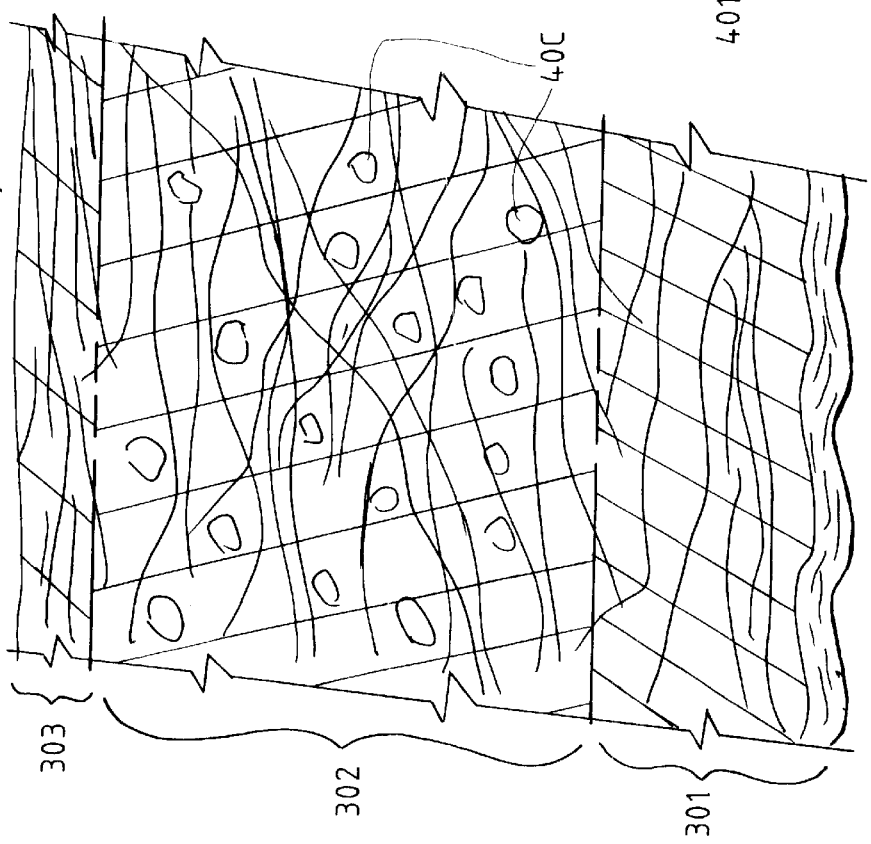
FIG. 4 is a view similar to FIG. 2, but FIG. 4 illustrates another form of absorbent material.

FIG. 4 illustrates a three-layer form of an absorbent material 300 that can be made by the process of the present invention and that is particularly well suited for use in feminine hygiene products. Such an absorbent material has a basis weight of from about 100 g/m² to about 250 g/m² and a density between about 0.25 g/cc and 0.5 g/cc. More preferably, the density is from about 0.3 g/cc to about 0.45 g/cc and, most preferably about 0.4 g/cc.

In one variation, the absorbent material 300 for use in a feminine hygiene product is air-laid as three layers or strata: a bottom layer 301 containing pulp (without superabsorbent) with a basis weight of about 25 g/m²; a middle layer 302 with a basis weight of about 150 g/m² and which contains from about 10 g/m² to about 30 g/m² superabsorbent 40C and from about 120 g/m² to about 140 g/m² pulp; and a top layer 303 containing pulp (without superabsorbent) with a basis weight of about 25 g/m². Relative to the total basis weight of the absorbent material 300, the level of superabsorbent 40C ranges from about 5 to about 15 weight percent (g/m² of superabsorbent per g/m² material). Preferably, the level of superabsorbent is from about 7.5 weight percent to about 12.5 weight percent of the absorbent material 300. Most preferably, the absorbent material 300 contains about 10 weight percent of superabsorbent. Thus, the middle layer 302 of the absorbent material 300 preferably contains from about 15 g/m² to about 25 g/m² superabsorbent and from about 125 g/m² to about 135 g/m² pulp and, more preferably about 20 g/m² superabsorbent and about 130 g/m² pulp. The middle layer 302 containing pulp and superabsorbent can be laid down as a homogeneous blend or as a heterogeneous blend wherein the level of superabsorbent varies with proximity to the bottom layer.

Figure 5:
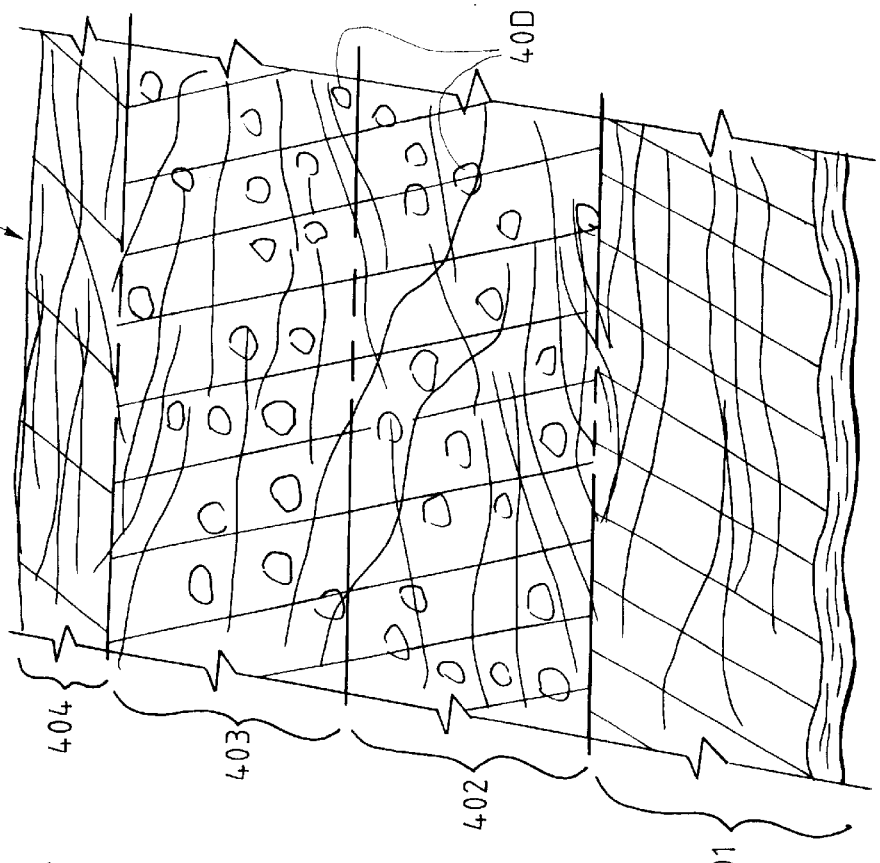
FIG. 5 is a view similar to FIG. 4, but FIG. 5 illustrates yet another form of an absorbent material.

FIG. 5 illustrates another form of an absorbent material 400 wherein the material is air-laid by the process of the present invention as four strata or layers: layer 401, layer 402, layer 403, and layer 404. The layers 402 and 403 may be characterized as two middle layers: a first middle layer 403 adjacent the top layer 404, and a second middle layer 402 adjacent the bottom layer 401. Each of the first and second middle layers independently comprises from about 10 to about 30 g/m² superabsorbent 40D and from about 40 g/m² to about 65 g/m² pulp. When it is desired to keep absorbed fluid away from the top of the feminine hygiene product (i.e., away from the surface of the article in closest proximity to the wearer) the amount of superabsorbent in the first and second middle layers 403 and 402 is adjusted such that there is a higher level of superabsorbent in the second middle layer. The superabsorbent in the first and second middle layers 403 and 403 can be the same or a different superabsorbent. The bottom layer 401 and top layer 404 do not contain any superabsorbent material.

Forms of Absorbent Material for Use in Diapers and Incontinent Products

In another variation, the absorbent material made by the process of the present invention is particularly well suited for use in diapers and incontinence products. Because such articles are expected to absorb and retain larger quantities of less viscous fluid than a feminine hygiene article, such an article employs absorbent material which is heavier and, thus, has a preferred basis weight of from about 350 g/m² to about 450 g/m². The overall composite density of that material is between about 0.3 g/cc and 0.5 g/cc. More preferably, the overall composite density is from about 0.25 g/cc to about 0.45 g/cc and, most preferably about 0.4 g/cc.

In a manner similar to that described above for a feminine hygiene product, a material suitable for use in diapers can be air-laid as one layer or multiple strata such as two, three, four, or more strata. When three strata are used (FIG. 4), the bottom layer 301 has a basis weight of about 50 g/m²; the middle layer 302 has a basis weight of about 300 g/m² and contains from about 40 g/m² to about 200 g/m² superabsorbent 40C and from about 100 g/m² to about 260 g/m² pulp; and the top layer 303 has a basis weight of about 50 g/m². Preferably, the middle layer contains from about 70 g/m² to about 170 g/m² superabsorbent and from about 130 g/m² to about 230 g/m² pulp. Even more preferably, the middle layer 302 contains about 80 g/m² superabsorbent and about 220 g/m² pulp or about 160 g/m² superabsorbent and about 140 g/m² pulp. The middle layer containing pulp and superabsorbent can be laid down as a homogeneous blend or as a heterogeneous blend wherein the level of superabsorbent varies with proximity to the bottom layer.

In a four strata variation (FIG. 5) used for diapers and adult incontinence products, the absorbent material 400 has two middle layers 403 and 403 which each independently contains from about 20 g/m² to about 100 g/m² superabsorbent 40D and from about 50 g/m² to about 130 g/m² pulp. In a preferred embodiment, the second (lower) middle layer 402 has a higher level of superabsorbent 40D than the first (upper) middle layer 403. In this way, the formed absorbent material 400 has a tendency to keep absorbed fluid away from the body surface of the wearer of the article. The superabsorbent 40D in the first and second middle layers 403 and 402 can be the same or a different material.

An absorbent material made by the process of the present invention can be incorporated into an absorbent article as a single-ply or multiple-ply structure. Means for forming such structures using folding are well known in the art. By way of example, a person skilled in art can "C-fold", "G-fold," or "Z-fold" the absorbent material prior to incorporating it into an absorbent article.

It will be readily apparent from the foregoing detailed description of the invention and from the illustrations thereof that numerous variations and modifications may be effected without departing from the true spirit and scope of the novel concepts or principles of the invention.

What is claimed is:

1. A process for making an absorbent material comprising the steps of:

(A) providing a carrier layer;

(B) forming a web having at least one layer of a mixture of cellulosic fibers and superabsorbent material on top of said carrier layer wherein at least some of said cellulosic fibers are provided by
  (1) treating a liquid suspension of pulp containing said cellulosic fibers at a temperature of from about 15° C. to about 60° C. with an aqueous alkali metal salt solution having an alkali metal salt concentration of from about 2 weight percent to about 25 weight percent of said solution for a period of time ranging from about 5 minutes to about 60 minutes, and
  (2) blending said cellulosic fibers and said superabsorbent material with controlled air circulation and mechanical agitation to form said mixture of cellulosic fibers and superabsorbent material free of chemical binding agents and heat set bonding agents;

(C) forming a layer of said cellulosic fibers which is free of said superabsorbent material and which is disposed on top of said at least one layer;

(D) increasing the moisture content of said web to increase the web density by conveying said web through a region into which steam having a temperature of above about 100° C. is discharged and maintaining the residence time of the web in said region for at least about 0.1 second; and (E) after step (D), compacting said web to less than about 3 mm at an elevated temperature to further increase the web density, to establish a web moisture content of between about 3% and about 10% as measured after cooling to ambient temperature, and to effect hydrogen bonding within the web, said step of compacting said web including the step of compacting said web between two calendering rolls wherein (1) at least one of the rolls is heated to a surface temperature in the range of between about 70° C. to about 180° C., (2) at least the roll contacting said carrier layer has a knurled surface to embed portions of said carrier layer in said at least one layer of a mixture of cellulosic fibers and superabsorbent material, and (3) the rolls exert a load of at least about 130 newtons per millimeter of transverse web width.

2. The process in accordance with claim 1 in which step (A) includes providing said carrier layer as a tissue layer; and step (B)(1) includes one of the following steps (a) and (b) prior to step (B)(2): (a) flash drying said cellulosic fibers, and (b) processing said cellulosic fibers through a hammermill.

3. A process for making an absorbent material comprising the steps of:

(A) treating a liquid suspension of pulp containing cellulosic fibers at a temperature of from about 15° C. to about 60° C. with an aqueous alkali metal salt solution having an alkali metal salt concentration of from about 2 weight percent to about 25 weight percent of said solution for a period of time ranging from about 5 minutes to about 60 minutes;

(B) blending said cellulosic fibers and superabsorbent material with controlled air circulation and mechanical agitation to form a mixture of cellulosic fibers and superabsorbent material free of added chemical binders and heat set bonding agents;

(C) forming a web having at least one layer of said mixture of cellulosic fibers and superabsorbent material;

(D) increasing the moisture content of said web to increase the web density; and (E) after step (D), compacting said web at an elevated temperature to further increase the web density and to effect hydrogen bonding within the web.

4. The process in accordance with claim 3 in which said step (A) includes forming said web with from about 10 weight percent to about 60 weight percent superabsorbent material; and said step (1) includes one of the following steps (a) and (b) prior to said step (2): (a) flash drying said cellulosic fibers, and (b) processing said cellulosic fibers through a hammer mill.

* * * * *